(12) United States Patent
Rösler et al.

(10) Patent No.: US 6,454,762 B1
(45) Date of Patent: Sep. 24, 2002

(54) INSTRUMENT FOR APPLYING LIGHT, ESPECIALLY LASER LIGHT, TO THE HUMAN OR ANIMAL BODY

(75) Inventors: Peter Rösler; Ronald Sroka, both of München; Andreas Leunig, Grünwald, all of (DE)

(73) Assignee: Karl Storz GmbH & Co. KG

( * ) Notice: Subject to any disclaimer, the term of this patent is extended or adjusted under 35 U.S.C. 154(b) by 64 days.

(21) Appl. No.: 09/626,330

(22) Filed: Jul. 26, 2000

Related U.S. Application Data

(63) Continuation-in-part of application No. PCT/EP99/00509, filed on Jan. 27, 1999.

(30) Foreign Application Priority Data

Jan. 27, 1998 (DE) ..................................... 298 01 223 U

(51) Int. Cl.[7] ............................................... A61B 18/22
(52) U.S. Cl. ............................ 606/15; 606/13; 606/14
(58) Field of Search .............................. 606/13, 14, 15

(56) References Cited

U.S. PATENT DOCUMENTS

| | | | |
|---|---|---|---|
| 4,313,431 A | 2/1982 | Frank | 128/7 |
| 4,881,524 A | 11/1989 | Boebel et al. | 128/6 |
| 5,209,747 A | 5/1993 | Knoepfler | 606/16 |
| 5,222,174 A | 6/1993 | Miles | 385/118 |
| 5,267,996 A | 12/1993 | Fletcher | 606/17 |
| 5,281,214 A | 1/1994 | Wilkins et al. | 606/15 |
| 5,425,355 A | * 6/1995 | Kulick | 600/183 |
| 5,807,235 A | * 9/1998 | Heff | 600/102 |

* cited by examiner

*Primary Examiner*—Lee Cohen
*Assistant Examiner*—Hank M. Johnson
(74) *Attorney, Agent, or Firm*—St. Onge Steward Johnston & Reens LLC

(57) ABSTRACT

An instrument is provided for applying light, particularly laser light, to the human or animal body. A tubular shaft is provided into which a flexible light waveguide may be inserted, where a light-emitting end of the waveguide comes to rest at a distal end portion of the tubular shaft. The distal end portion of the tubular shaft is pivotally connected with the remaining portion of the tubular shaft, so that the distal end portion may be pivoted away from the longitudinal axis of the tubular shaft. Manipulating devices are provided at the proximal end of the tubular shaft for pivoting the distal end portion. The manipulating devices include at least one movable operating element, which is directly connected to the distal end portion by means of an actuator element.

29 Claims, 4 Drawing Sheets

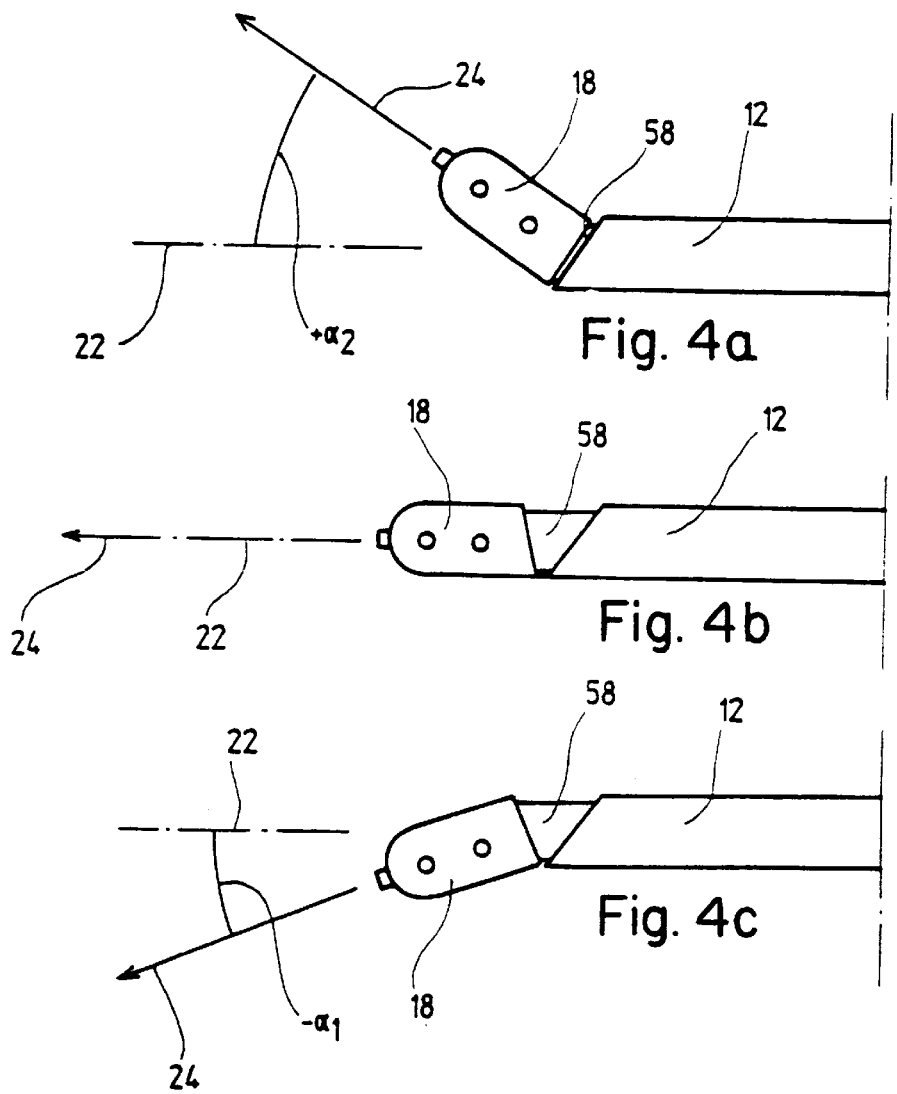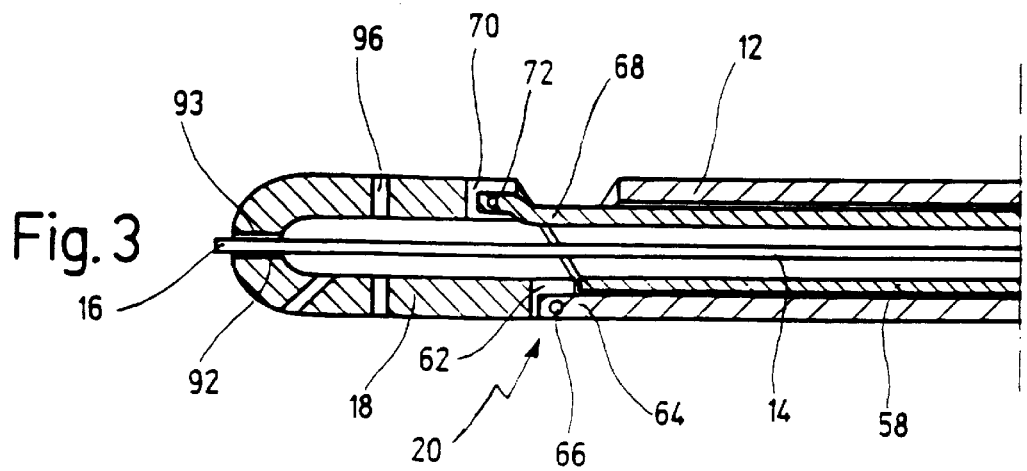

INSTRUMENT FOR APPLYING LIGHT, ESPECIALLY LASER LIGHT, TO THE HUMAN OR ANIMAL BODY

CROSS REFERENCE TO PENDING APPLICATION

This is a continuation-in-part of pending International application PCT/EP99/00509 filed Jan. 27, 1999, which designated the United States.

BACKGROUND OF THE INVENTION

The invention relates to an instrument for applying light, particularly laser light, into the human or animal body, especially for endonasal laser surgery.

In the medical field relating to respiratory organs, patients must be frequently treated when respiration is hindered in the nose. The most common cause for respiratory problems in the nose are pathological enlargements in the upper, central and/or lower concha of the inner nose. The condition of pathologically enlarged concha is distinguished between hypertrophy and hyperplasia of the concha.

Hypertrophy is an increased concha volume resulting from the swelling of cells, which is caused by an allergy or is hereditary. It does not represent a true growth of tissue. The condition of hyperplasia is a cell multiplication initiated by the body, which is an actual cell tissue growth. The purpose of the treatment in both cases is to improve respiration by reducing the concha of the nose.

Various therapeutic methods have been developed in the background art. Conventional methods include diathermy, for example high frequency heat therapy or electro-coagulation, and conchotomy by which part of the concha is cut out with a mechanical cutting instrument.

With respect to diathermy, a disadvantage is that the depth of the heat treatment is difficult to control. In addition, large portions of the mucous membrane can be damaged. Further side effects can occur in the early post-operative phase, for example the feeling of illness and disturbed respiration.

Conchotomy has the disadvantages that the therapy must be carried out under full narcosis, that strong bleeding is caused and the use of tampons is necessary due to the danger of subsequent bleeding. In addition, conchotomy requires stationary treatment of four to seven days and a longer convalescence time. Furthermore, the danger of improper healing and infection exists.

The treatment of pathological tissue by means of laser light, which has been successful in other medical fields, is not hampered with the above-mentioned disadvantages. In contrast to the above conventional operation methods, a therapy with laser light allows a minimal invasive operation. The possible advantages of laser therapy of the concha have been reported in the German medical journal "HNO aktuell", pages 223 to 230, 1997 in the article "Laser in der Rhinologie". The actual use of laser therapy for treating the concha, however, has failed to date due to the lack of suitable instruments. The effect of laser light on tissue in general includes a coagulation, i.e. a heating, by which the tissue protein is denaturated, and an ablation and vaporization, by which tissue is removed or vaporized.

The effect depends on the distance from the waveguide tip to the tissue through which the applied energy density can be varied. The "contact method" and the "non-contact method" have become common. In the contact method, the waveguide tip contacts the tissue achieving a vaporizing, cutting effect. In the non-contact method, a defined spacing exists between the waveguide tip and the tissue to be treated, where an ablation or coagulation of the tissue takes place.

The advantages of laser therapy are numerous. The risk of bleeding is substantially reduced, the operation time is greatly shortened, no full narcosis is necessary but only a local narcosis and post-operative complications are extremely unlikely.

In using laser light therapy for reducing the lower concha, instruments are currently being used on a trial basis, which have become established in orthopedics for laser arthroscopy. These instruments consist of a simple, bent tube, which receives the light waveguide. The tube or tubular shaft is previously bent to an angle of up to 30° or is bent after insertion corresponding to the given anatomy of the patient.

These known instruments, however, have several drawbacks. When inserting the waveguide, the tip and especially the polished end surface where light emission takes place can be damaged when passing the bent section of the tube. The emission end surface of the waveguide can become split. The consequence of damaging the emission surface of the waveguide is that laser light is beamed sidewards in uncontrolled manner. Thus there is a danger that non-participating tissue would be damaged by uncontrolled laser light, which would thus injure the patient. In addition, the doctor treating the patient could become injured by the uncontrolled emission of laser light.

A further drawback of the known instruments is that the bent tube allows only one fixed operation angle, i.e. a fixed emission direction of the laser light, which is insufficient for the individual anatomy of respective patients. Since the beam direction is adjusted by bending the tube, the tube may not be usable over longer time periods due to material fatigue.

Another drawback of the known instruments is that once having made the adjustment of the beam direction during the treatment, it can no longer be varied. To readjust the direction, the tube must be removed from the operation area and correspondingly re-directed to a new position, whereby the operation time is substantially increased. The manipulations are thus impractical.

The known instruments are therefore not suitable for applying laser light for reducing the concha. The invention on the other hand is not limited to this field of application. Rather, it is basically applicable to all medical fields where a guidewave is inserted into small body cavities or passages and where therapeutic light is to be accurately directed to a point on tissue to be treated, in particular where there is very little space. Examples include arthoscopy, urology, laparoscopy, neurosurgery, etc.

U.S. Pat. No. 4,881,524 mentioned above discloses an instrument for guiding a laser light transmitting fiber in intra-abdominal endoscopic work, wherein this known instrument comprises a shaft to the distal end of which is pivoted a fiber guide for deflecting the distal end of a fiber emerging from the distal end of the shaft. The shaft contains a fiber guide drive tube through which the fiber extends and which is articulated to the fiber guide by means of a link. A lever is provided for shifting the drive tube axially in the shaft to deflect the fiber guide and thus the distal end of the fiber, and a fiber feed device has a fiber feed member mounted for displacement axially of the shaft for advancing and retracting the fiber.

The disadvantage of this known instrument is that the light-emitting end of the waveguide fiber can only be pivoted in one direction out of the longitudinal axis of the shaft. Thus, the working range of this known instrument is restricted.

The invention, however, is not limited to medical applications, but can also be employed in technical applications.

The object of the present invention is then to provide an instrument of the mentioned type, which avoids the above draw-backs and by which a light waveguide for applying light, in particular laser light, can be directed to a difficultly accessible position, where light emission is possible with simple handling in several directions.

SUMMARY OF THE INVENTION

According to the present invention, an instrument for applying light, particularly laser light, into the human or animal body, in particular for endonasal laser surgery, is provided, comprising:

- a tubular shaft having a proximal end and a distal end portion, said distal end portion being pivotally connected to a remaining portion of said tubular shaft;
- a light waveguide being insertable into said tubular shaft, said light waveguide having a distal light-emitting end which comes to rest in said distal end portion of said tubular shaft;
- a manipulating means disposed at said proximal end of said tubular shaft, said manipulating means having at least one movable operating element operatively connected with said distal end portion via an actuator element for pivoting said distal end portion out of a longitudinal axis of said shaft, wherein said distal end portion is pivotably connected to said remaining portion of said tubular shaft by a joint which allows pivotal motion of said distal end portion in opposite direction in a range between an angle $-|\alpha_1|$ and an angle $+|\alpha_2|$ with respect to said longitudinal axis of said tubular shaft.

As opposed to the instruments of the prior art, which have a flexible tube or flexible tubular shaft, the present instrument provides for the distal end portion including the light emission end of the waveguide or its tip to be pivotally connected with the remaining portion of the tubular shaft. The shaft is thus formed of at least two parts, the distal end portion and the remaining portion with a pivotal joint connection there-between. In the simplest case, the distal portion can be connected to the remaining shaft via a flexible elastic element, for example a spring, in particular a leaf spring. The distal end portion is thus pivotable out of the longitudinal axis of the shaft about a defined axis.

A considerable advantage is that the waveguide can be inserted in the shaft when the distal end portion is aligned in a straight line with the remaining portion of the shaft. In this 0° position of the distal end, the waveguide can be inserted up to the outermost distal end of the shaft without the danger of damaging the emission end surface. The shaft with the inserted waveguide can then be passed into the nose, for example for endonasal laser surgery. By operating at least one movable handling element of the manipulating means, the distal end portion of the shaft and thus the emission surface of the waveguide can be pivoted about the defined pivot axis to thereby direct the laser light beam with high accuracy onto the tissue area to be treated. The operator can change the direction of the laser beam without having to remove the instrument from the operation area, which greatly facilitates use of the present instrument.

Due to the pivot connection of the distal end with the remaining portion of the shaft, a material fatigue caused by bending cannot occur as in the known instruments. The instrument according to the present invention thus allows a safe, accurate guidance of the laser beam in the operation area without the danger of damaging or injuring non-participating tissue. When applying laser therapy for reduction of the concha by vaporization and ablation of tissue, an immediate respiratory relief occurs post-operatively. The respiratory passage in the inner nose is additionally enlarged in the following healing of the coagulated tissue, where further tissue is discarded.

Further, the joint enables a pivotal motion of the distal end in an angular range between an angle of $-\alpha_1$ and an angle $+\alpha_2$ with respect to the axis of the shaft. The advantage is that the distal end portion of the shaft and therefore the emission direction of the light beam can be angled toward both sides of the longitudinal axis of the shaft, when both $\alpha_1$ and $\alpha_2$ are different from zero. This is possible without having to change the position of the entire instrument, in particular the position of the manipulating means by the operator. The angle $-\alpha_1$ can be between 0° and −90° or more and the angle $+\alpha_2$ can also be between 0° and +90° or more. The maximum angle is limited by the maximum allowable bending of the waveguide on the one hand and by the conditions for total reflection in conducting the light in the waveguide on the other hand.

In a preferred embodiment the joint is a hinge-like joint.

An advantage is that the hinge joint provides a stable pivotal connection between the distal end and the remaining shaft, because no parts need be employed which are subject to bending load or bending stress.

The angles $|\alpha_1|$ and $|\alpha_2|$ depend on the application for which the instrument is used.

In a further preferred embodiment, the tubular shaft as a whole or at least a portion of the shaft secured to the distal end portion is rotatable with respect to the manipulating means about the longitudinal axis of the shaft.

The rotation in conjunction with the pivotability of the distal end portion enables angular placement of the light beam in three-dimensional angular space and thus further enhances the variability of the instrument. To rotate the tubular shaft, an adjustment wheel can be provided on the manipulating means, which allows easy rotation of the shaft. The shaft can also be further sub-divided with a rotary coupling.

It is further preferred if the distal end portion is formed as a tube piece which is directly adjacent to the remaining portion of the tubular shaft.

The advantage of this feature is that the distal end portion and the remaining portion of the tubular shaft can form a substantially tight arrangement so that the risk of contamination of the interior of the tubular shaft is reduced.

In this context, it is preferred if the distal end portion and the remaining portion of the tubular shaft form a V in the region of the joint, wherein at a tip of the V the joint connection is established.

This kind of connecting the distal end portion with the remaining portion of the tubular shaft advantageously allows an arrangement of the distal end portion as close as possible to the remaining portion of the shaft on the one hand, and further allows pivotal motion of the distal end portion in opposite directions out of the longitudinal axis of the tubular shaft, on the other hand.

In a further preferred embodiment, the distal end portion has an axial length, which is only slightly larger than the outside diameter of the remaining shaft.

This is of advantage when using the instrument according to the present invention in very small operation areas, for example in small channel-like body passages, because then pivoting of the distal end portion by a larger angle is not hindered by the small space in the operation area.

In a further preferred embodiment, the distal end portion has substantially the same outer diameter as the remaining portion of the tubular shaft.

The advantage is that when inserting the shaft into the operation area no radial divergence is present between the distal end and the remaining portion of the shaft, which if present could lead to mechanical injury of tissue upon insertion or could hinder insertion of the instrument.

It is to be understood that for applications of the instrument according to the present invention for endonasal surgery it is preferred if the outer diameter of the tubular shaft is small, for example in a range between 2 and 10 mm.

In a further preferred embodiment, the distal end portion comprises a fixing sleeve for fixing the light-emitting end of the light waveguide.

The advantage is that the light-emitting end of the waveguide has no radial and/or axial play in the distal end portion, which could hinder an accurate application of the laser light to a point. With this configuration, the accuracy of guidance of the light beam is improved.

In a further preferred embodiment, the tubular shaft comprises a connector for connecting a suction and/or irrigation means to the tubular shaft, wherein it is further preferred if the interior of the tubular shaft comprises a suctioning and/or irrigating passage even when the waveguide is present. This has the advantage that a possibility is provided for suctioning off gases or vapors, which may arise from the vaporization of tissue, may be toxic and may hinder visibility. The gases can be safely removed from the operation area via the tubular shaft. By introducing an irrigation fluid, the operation area can be washed, whereby good visibility with an additional endoscope for endoscopic control of the operation can always be maintained. For the suctioning and irrigating operations, two separate connectors can also be provided.

In a further preferred embodiment, the pivotal distal end portion comprises openings distributed about its circumference for suctioning and/or irrigating.

The advantage is that the suctioning off of gases, fluid and tissue pieces as well as the irrigating of the operation area can take place through the distributed openings on all sides about the distal end portion.

In this context, it is further preferred if the openings mentioned before are disposed at a front face and at axially extending sides of said distal end portion.

In a further preferred embodiment, the manipulating means are configured in the form of a scissor-like handle arrangement.

Such manipulating means are particularly advantageous because the doctor is already accustomed to such arrangements in medical devices including forceps, scissors and the like. Guiding the laser light beam in the operation area can therefore be handled by the doctor just as reliably as for example in making an incision with a medical forceps. In other words, this configuration provides a "laser forceps".

In a further preferred embodiment, the actuator element is configured as a wire or rod-like push and pull element, which runs through the interior of the tubular shaft.

This provides a constructively simple actuator with direct mechanical connection between the pivotal distal end portion and the manipulating means. The wire or rod-like push and pull element is preferably arranged in the interior of the shaft so as not to enlarge the outer dimensions of the instrument.

In a further preferred embodiment, the actuator element is formed as an inner tubular shaft arranged to be axially shiftable within the tubular shaft, with the waveguide being insertable in the interior of the inner tubular shaft.

This arrangement of the actuator element has the advantage that it is very stable and reliably responsive to both pushing and pulling. The embodiment also leads to a particularly small radial dimension of the instrument with a double tubular shaft. Since the inner shaft is designed for guidance and reception of the waveguide, it can be very easily inserted. Compared to the above-mentioned wire-like push and pull element, the actuator element being an inner tubular shaft reliably avoids complications and hindrances when inserting the waveguide into the shaft. A further advantage of this embodiment is that more space is available for the suction and/or irrigation passage in the interior of the tubular shaft or in the interior of the inner tube shaft, so that not only gases and liquids can be with-drawn, but also small pieces of tissue.

In a further preferred embodiment, the actuator element is articulated to the distal end portion at an articulation point which is radially spaced from the joint of the distal end portion by a distance which is substantially equal to the outer diameter of the tubular shaft.

The advantage of this arrangement is that the largest possible lever between the articulation point and the joint is formed which advantageously uses the full diameter of the tubular shaft.

In a further preferred embodiment, the pivotal motion of the pivotal distal end is limited to a predetermined angular range.

Limiting the pivotal motion has the advantage that the maximal pivotability of the distal end portion can be adapted to the given waveguide being employed. In this manner, breaking the waveguide by overbending can be avoided.

In a further preferred embodiment, the limit of pivotal motion can be adjusted by an adjustable stop on the manipulating means.

Instead of limiting the pivotal motion directly at the pivot connection of the distal end with the remaining portion of the shaft, this feature has the advantage that the joint connecting the distal end with the remaining portion can be configured so that a pivoting over an angular range of about −90° to +90° is in principle possible. The pivoting is then limited by the stop on the manipulating means by limiting the travel path of at least one movable operating element. Thus the limitation of the pivot range of the distal end portion can be adapted to the respective waveguide employed by the adjustability of the stop.

In a further preferred embodiment, the distal end portion can be locked in a plurality of discrete or continuous angular positions with respect to the longitudinal axis of the tubular shaft.

This provides certainty in the adjustment of the distal end portion, which further improves the reliably accurate application of the laser beam, because it prevents a previously defined beam direction of the laser light from being inadvertently readjusted.

It is further preferred that the at least one movable operating element of the manipulating means be engageable with a toothed bracket having a plurality of catch or lock positions.

This has the advantage that a constructively simple and easily operable setting means is provided for a plurality of defined angular positions of the distal end and therefore a setting of the beam direction of the laser light. When the movable operating element is disengaged from the toothed bracket, the distal end portion of the shaft can also be adjusted continuously. This feature has the advantage that the angular position of the distal end can be varied in discrete steps without releasing the adjustment securement, so that the handling is further simplified. A further advantage is that changing the angular position takes place substantially without shock.

In a further preferred embodiment, the distal end of the pivotal distal end portion is rounded.

The advantage is that mechanical injury of the tissue is avoided when introducing the shaft into the operation area, in particular the mucous membrane in the case of endonasal laser surgery.

Further advantages of the present invention will become apparent in the following description taken in conjunction with the attached drawings. It will be understood that the above features and those to be discussed below are not only applicable in the given combinations, but may also be used in other combinations or taken alone without departing from the scope of the present invention.

Embodiments of the present invention are illustrated in the drawings and will be discussed in more detail below.

BRIEF DESCRIPTION OF THE DRAWINGS:

FIG. 3 shows a greatly enlarged representation of the distal end of the instrument in FIG. 1 in cross-section.

FIGS. 4a to 4c show enlarged illustrations of the distal end of the instrument in FIG. 1 in various angular positions of the distal end portion.

DETAILED DESCRIPTION OF PREFERRED EMBODIMENTS

Figure 1:
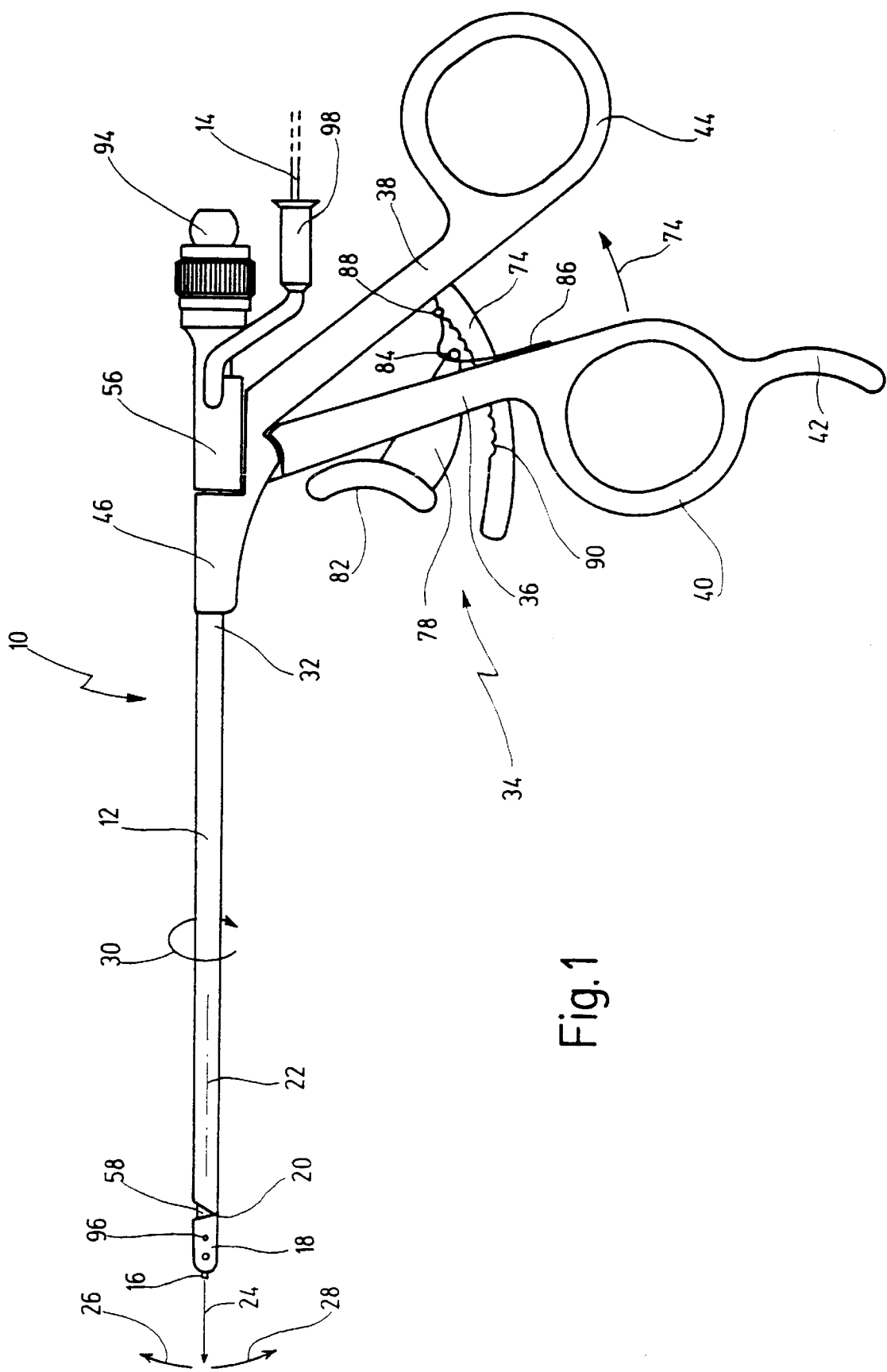
FIG. 1 shows a side view of a first embodiment of the instrument for applying light according to the present invention.

FIG. 1 illustrates an instrument for applying light, especially laser light, into the human or animal body which is generally designated with numeral 10. Instrument 10 is employed for example in endonasal laser surgery for reduction of pathologically enlarged concha in the nose. The instrument however is not limited to such applications, but can be used in other medical fields, for example orthopedics, urology, etc. Instrument 10 can also be used in technical applications. In principle the instrument 10 may be used in all areas where light, particularly laser light, is to be guided to difficultly accessible locations.

Instrument 10 comprises an extended tubular shaft 12. The shaft 12 is small with respect to its outer diameter, so that it can be used in endonasal laser surgery and can be introduced into the nose with an endoscope. Further, the shaft 12 extends along a straight line. The outer diameter of the shaft 12 may be in the range of 2 to 10 mm.

A flexible light waveguide 14 can be inserted into the shaft 12, where the distal light emitting end 16 or the tip of the waveguide 14 comes to rest at the distal end portion 18 of the shaft 12. The waveguide 14 is preferably an optical fiber having a diameter of less than 1 mm, for example in bare fiber or sidefire fiber configuration.

Although the light emitting end 16 of the waveguide 14 in FIG. 1 is shown to extend from the distal end portion 18, the tip 16 can also be disposed flush to the distal end of the distal end portion 18.

The distal end portion 18 is formed as a tube piece which is disposed directly adjacent to the remaining portion of the tubular shaft 12.

The distal end portion 18 of the tubular shaft 12 is pivotally connected to the remaining portion of the shaft 12 by a joint 20, so that the distal end portion 18 may be pivoted out of the longitudinal axis 22 of the two-part shaft 12. Joint 20 is a hinge-like joint, which will be described in more detail below.

As may be seen in FIGS. 1 and 4, the distal end portion 18 and the remaining portion of the shaft 12 form a V in the region of the joint 20. The joint 20 is disposed at a tip of the V-like connection.

The pivot axis of the joint 20 runs transverse to the longitudinal axis 22 of the shaft 12. By pivoting the distal end portion 18, the light emitting end 16 of the waveguide 14 is pivoted to adjust the beam direction of the emitted light as shown by the arrows 26, 28. The beam direction 24 thus can take on various continuously changeable angle positions with respect to the axis 22 of the shaft 12. The shaft 12 is also rotatable about its axis 22 as indicated by the arrow 30. In this manner, the distal end portion 18 is not only pivoted in the plane of the drawing in FIG. 1, but also into all planes not parallel thereto by rotation of the shaft 12. The beam direction 24 can thus be varied in any spatial angular region.

To rotate the shaft 12, an adjustment wheel can be arranged about the shaft 12 at a position indicated with numeral 32, which is fixed to the shaft 12. To pivot the distal end portion 18, the instrument 10 comprises manipulating means generally designated with numeral 34 at the proximal end of the shaft 12, which will be discussed in detail below in conjunction with FIGS. 1 and 2. The manipulating means 34 are configured in the form of a scissor-like handle arrangement. The manipulating means 34 comprise a movable operating element 36 as well as a stationary operating element 38. The movable operating element 36 comprises a ring 40 for the middle finger and an ergonomically formed support piece 42 for the ring finger of the same hand. The stationary supporting element 38 includes a ring 44 for receiving the thumb. The manipulation arrangement including the movable element 36 and the stationary element 38 enable a particularly ergonomic handling of the instrument 10.

The stationary operating element 38 comprises a sleeve-like portion 46 in which the proximal end 48 of the shaft 12 is secured for rotation about the longitudinal axis 22, so that the shaft 12 is rotatable with respect to the operating element 36 and 38. The movable operating element 36 is connected to the stationary operating element 38 via a joint 50. The end 52 of the movable operating element 36 opposed to the support 42 has a fork-like structure and engages a pin 54, which is secured to a carrier 56 being axially shiftable relative to the shaft 12.

To transmit force from the movable operating element 36 to the distal end portion 18 of the shaft 12, an actuator element is provided in the form of an inner tubular shaft 58, which is arranged to lie adjacent to the inner wall of the tubular shaft 12. The proximal end 60 of the inner shaft 58 is received by the sleeve-like carrier 56 and fixed thereto. The inner shaft 58 is axially shiftable with respect to the shaft 12 and extends to the distal end portion 18 of the shaft 12.

Referring to FIG. 3, the distal end portion 18 of the shaft 12 comprises a proximal bifurcated section 62 in which an axial projection 64 engages. The projection 64 is connected with the bifurcated section 52 by means of a link pin 66 and forms the joint 20.

The actuator element in the form of the inner tubular shaft 58 comprises an axial projection 68, which engages in another bifurcated section 70, lying opposed to the bifurcated section 62 of the distal end portion 18, and is pivotally connected thereto via a further link pin 72. Actuator element 58 is pivotally connected to the distal end portion 18 at link pin 72, which is radially spaced from joint 20 by a distance which is substantially equal to the outer diameter of shaft 12.

By actuating the movable operating element 36 in the direction of the arrow 74 in FIG. 1, the carrier 56 and the inner shaft 58 fixed thereto are shifted in the direction toward the distal end, whereby the distal end portion 18 is pivoted in the direction of the arrow 28. By moving the movable operating element 36 in the counter-direction of arrow 74, the distal end portion 18 correspondingly pivots in the direction of the arrow 26.

Referring to FIGS. 4a to 4c, the distal end portion 18 and therefore the beam direction 24 can take on angular positions with respect to the axis 22 of the shaft 12 in a range between an angle $+|\alpha_2|$ to an angle of $-|\alpha_2|$. The angle $+|\alpha_2|$ and $-|\alpha_1|$ can have the same magnitude or different magnitudes. In the illustrated example, the angle $+|\alpha_2|$ is about 50° and the angle $-|\alpha_1|$ is about -10°. The invention however is not limited to this angular range. The maximal values of $\alpha_1$ and $\alpha_2$ can also be 90° or more, whereas $\alpha_1$ could also be 0°.

Figure 2:
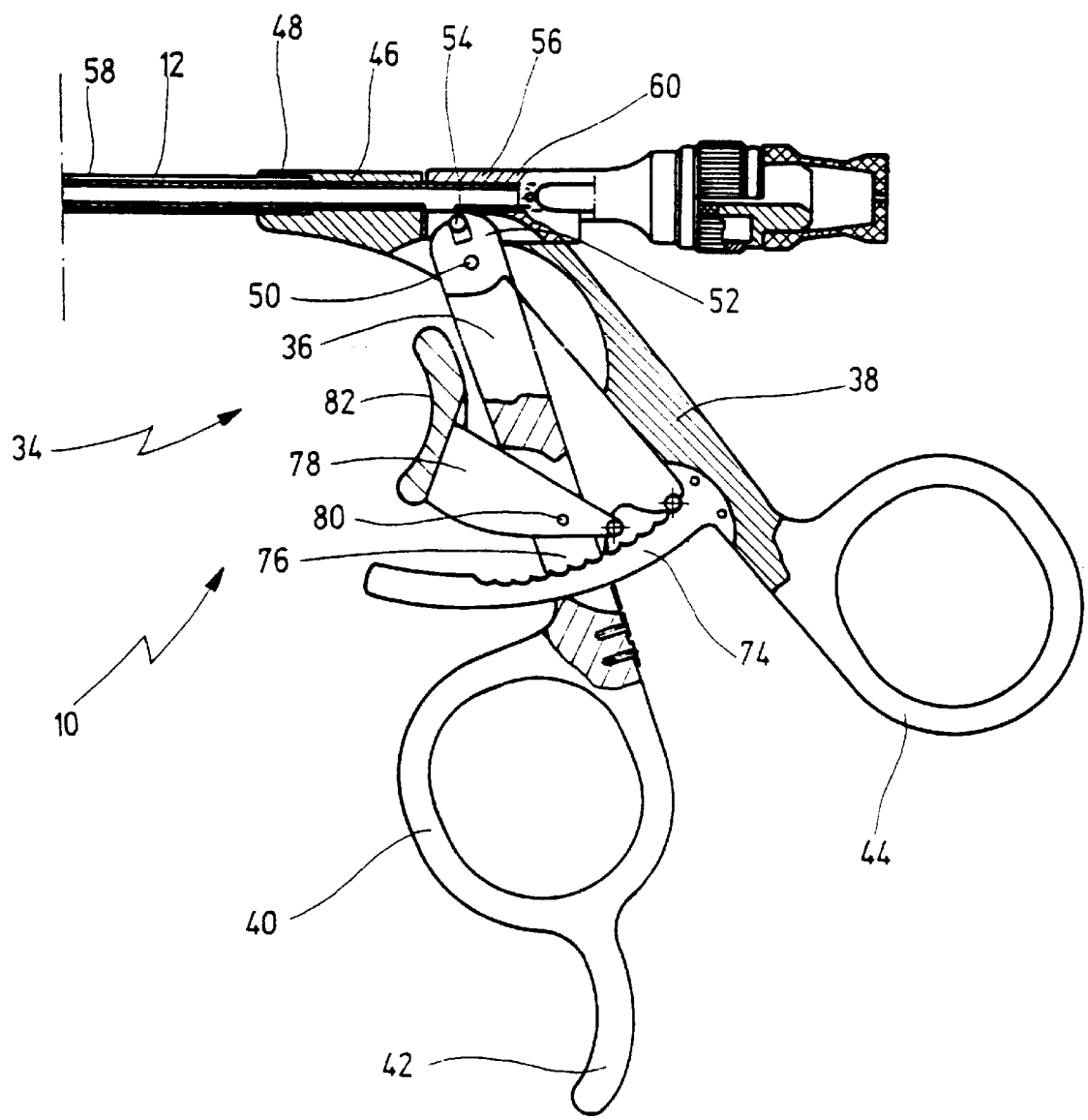
FIG. 2 shows a partially cut-away side view of the proximal end of the instrument in FIG. 1.

According to FIGS. 1 and 2, the stationary operating element 38 includes a toothed bracket 74, which passes through a bifurcated or slotted section 76 of the movable operating element 36, so that the movable operating element 36 is translated with respect to the bracket 74. In addition, a rocker 78 is arranged in the bifurcated section 76 of the movable operating element 36 and rotatably mounted via a joint 80. The rocker 78 comprises a curved support surface 82 for operation with the index finger of the same hand that holds the instrument 10. On the end opposing the support surface 82, the rocker 78 comprises a pin 84, which engages behind a leaf spring 86 secured to the movable operating element 36 in looped manner. At its outer free end, the leaf spring 86 comprises a roller 88, which can be brought into and out of engagement with the teeth 90 of the bracket 74. By rotating the rocker 78, more precisely the support surface 82, upwardly, the roller 88, biased downwardly by the leaf spring 86, comes into engagement with the toothed bracket 74. By rotating the rocker 78 in the opposite direction, the pin 84 urges the free end of the leaf spring 86 upwardly, whereby the roller 88 releases engagement with the toothed bracket 74.

By means of the toothed bracket 74 it is possible to lock the distal end portion 18 of the shaft 12 in a plurality of discrete angular positions. When the roller 88 is disengaged with the bracket 74, the distal end portion 18 is continuously pivotable. The teeth 90 of the toothed bracket 74 are preferably rounded at their tips, so that the engagement of the roller 88 with the toothed bracket 74 allows a pressure-free pivotal movement of the distal end portion 18 in discrete steps.

The maximal angle $+\alpha_2$ or $-\alpha_1$ according to FIG. 4 can be adjusted through a stop not shown in FIG. 1. The stop is located between the movable operating element 36 and stationary operating element 38 and is adapted to the properties of the waveguide 14.

As shown in FIGS. 1, 3 and 4, the distal end of the distal end portion 18 is rounded. The axial length of the distal end portion 18 is preferably only slightly larger than the outer diameter of the shaft 12. The outer diameter of the distal end portion 18 is preferably the same as the outer diameter of the remaining portion of the shaft 12, so that the transition region has no radial discrepancy between the distal end portion 18 and the remaining portion of the shaft 12.

The distal end portion 18 further comprises a fixing sleeve 92 so that the tip 16 of the waveguide 14 is at least radially but also axially fixed in the distal end portion 18. As seen in FIG. 3, the distal end portion 18 comprises an axial bore 93 at its distal end in which the tip 16 of the waveguide 14 is fixed in the fixing sleeve 92 substantially without play.

As seen in FIG. 1, the proximal end of the tubular shaft 12 includes a connector 94 for connecting the shaft 12 with a suction and/or irrigation means (not shown). As seen in FIG. 2, an adaptor piece of the suction and/or irrigation hose can be attached to the connector. The suctioning or irrigating takes place through the interior of the inner tubular shaft 58, which also receives the waveguide 14. As seen in FIG. 3, a cross-sectional area or passage remains for suctioning and irrigating. Two separate connections can also be provided for suctioning and irrigating. Bore openings 96 are distributed about the circumference of the distal end portion 18 and serve as suction or irrigating openings. The openings 96 are distributed at a front face as well as at axially extending sides of the distal end portion 18.

In the following, an operative laser-surgical method is described, which is performed with the instrument 10, namely for laser treatment of the concha in the nose. First of all, the waveguide 14 is passed from the proximal end of the shaft 12 through an inlet opening 98. The inlet opening 98 is joined to the proximal end 60 of the inner tubular shaft 58, so that the waveguide 14 can be passed through the inner tubular shaft 58. The waveguide 14 is pushed further until the light-emitting end 16 comes to rest in the distal end portion 18 of the shaft 12. By inserting the waveguide 14, the distal end portion 18 is brought into 0° alignment with the longitudinal axis 22 of the shaft 12 by means of the movable operating element 36. With this, possible damage to the tip of the waveguide 14 is avoided.

The opposite end of the waveguide is coupled to a suitable laser. The parameters of the laser are correspondingly adjusted. The tip 16 of the waveguide 14 is then guided and positioned into the operation area. At the same time, an optical endoscope is introduced into the nose for observation of the positioning procedure and the subsequent operation.

A precise positioning of the tip or the light-emitting end 16 of the waveguide 14 and thus the beam direction 24 is under-taken by actuating the movable operating element 36 and by rotating the shaft 12. After the tip is properly positioned, the concha to be treated is irradiated back and forth in lines. This can be accomplished by pivotal movement of the distal end portion 18 and thus the beam direction 24 in discrete or continuous manner. During the treatment, gases can develop due to vaporization or coagulation of the tissue. These are drawn out through the inner tubular shaft 58 via the suction means. In addition, the operation area can be irrigated by introducing an irrigation fluid through the tubular shaft 12 or the inner tubular shaft 58, in order to allow endoscopic visual control during the operation or to cool the operation area.

The treatment of the tissue can be performed in the mentioned contact method or the non-contact method. A combination of the two techniques can also be employed. Due to the angular adjustability of the tip 16 of the waveguide 14 by pivoting the distal end portion 18 of the shaft 12, the treatment can be repeated several times or at other locations without intermediate withdrawal of the instrument from the operation area.

Figure 5:
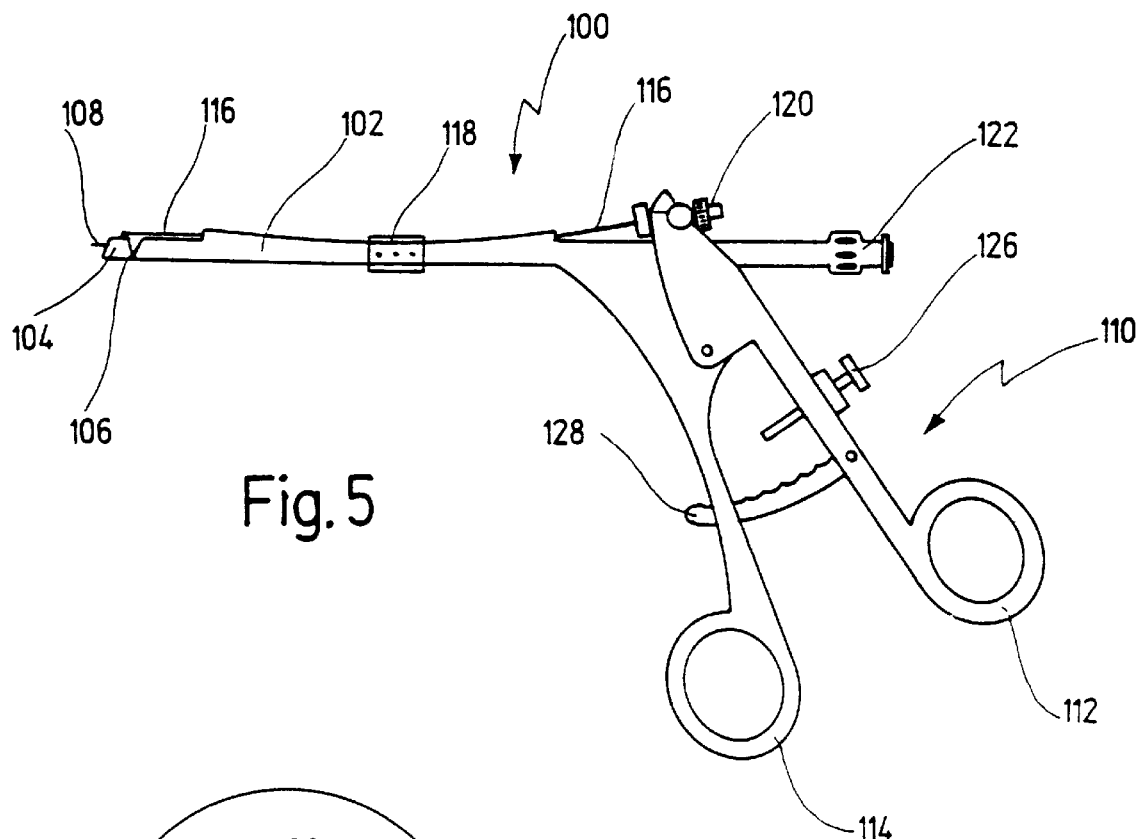
FIG. 5 shows a side view of a further embodiment of the instrument according to the present invention.
Figure 7:
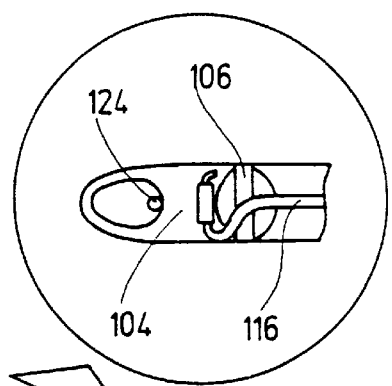
FIG. 7 shows an enlarged representation of the distal end of the instrument in FIG. 6.
Figure 6:
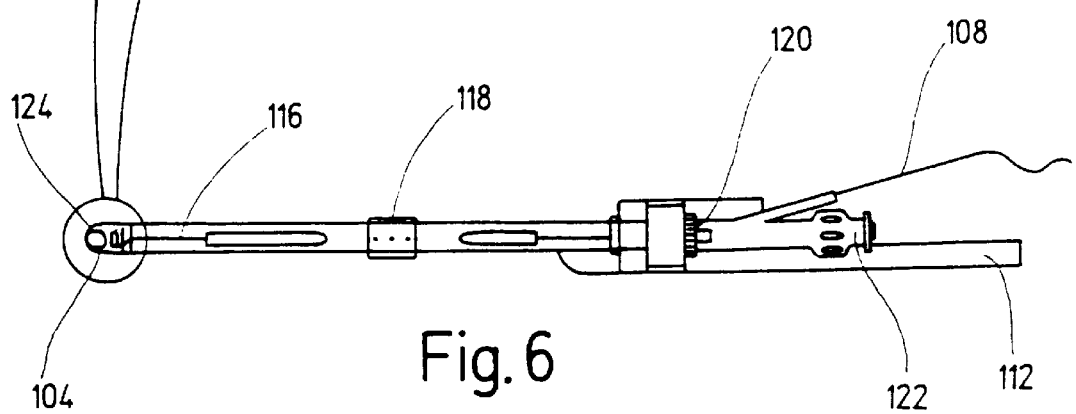
FIG. 6 shows a plan view of the instrument in FIG. 5.

Finally, FIGS. 5 to 7 show a further embodiment of the instrument 100, which differs only slightly from the instrument 10. The instrument 100 again comprises a two-part tubular shaft 102 with a distal end portion 104, which is connected to the remaining portion of the shaft 102 via a joint 106 in the form of a hinge. The shaft 102 is adapted to receive a light waveguide 108 therein.

A manipulating means 110 is provided to pivot the distal end portion 104, which includes a movable operating element 112 and a stationary operating element 114, which is fixed to the tubular shaft. An actuator element in the form of a cable or wire-like push and pull element 116 connects the movable operating element 112 for direct actuation with the distal end portion 104 of the shaft 102. The push and pull element 116 runs partially through the tubular shaft 102.

The remaining proximal portion of the shaft 102 is rigid and may have a straight line shape or a curvature with an angle of about 5°. The tubular shaft 102 includes a further sub-division in the form of a rotatable coupling piece 118, so that that portion of the shaft 102 is rotatable which is connected to the distal end portion 104. In this manner, the tubular shaft 102 can be rotated about its longitudinal axis by 360°.

The push and pull element 116 is secured by spanning means 120 to the movable operating element 112. The spanning means 120 makes it possible to connect the push and pull element 116 with a suitable biasing toward the distal end portion 104 of the tubular shaft 102.

The tubular shaft 102 is also formed with a suction channel for gas, ablation products, tissue, fluids, and an irrigation channel. For this purpose, the proximal end of the tubular shaft of 102 is provided with connector 122 for connecting a suctioning and/or irrigation device. Two separate connectors can be provided for suctioning and irrigating.

The light waveguide 108 is held at its distal end in a fixing sleeve 124, arranged in the distal end portion 104. The angular adjustment of the distal end portion 104 is limited to avoid overbending of the glass fiber or the waveguide 108 by means of an adjustable stop 126, which is secured to the operating element 112.

A grated or toothed bracket 128 serves to lock or to secure the adjustment of the angular position of the distal end portion 104. With this, the adjusted angle of the distal end portion 104 and thus the distal end of the waveguide 108 is fixed.

The instrument 100 differs the instrument 10 only in the form of the push and pull element 116 as the actuator element and the interchanged arrangement of the movable operating element 112 and the stationary operating element 114.

What is claimed is:

1. An instrument for applying light into the human or animal body, comprising:
   a tubular shaft having a proximal end and a distal end portion, said distal end portion being pivotally connected to a remaining portion of said tubular shaft;
   a light waveguide being insertable into said tubular shaft, said light waveguide having a distal light-emitting end which comes to rest in said distal end portion of said tubular shaft;
   a manipulating means disposed at said proximal end of said tubular shaft, said manipulating means having at least one movable operating element operatively connected with said distal end portion via an actuator element for pivoting said distal end portion out of a longitudinal axis of said shaft,
   wherein said distal end portion is pivotably connected to said remaining portion of said tubular shaft by a joint which allows pivotal motion of said distal end portion in a first direction from an angle of zero degrees to an angle $-|\alpha_1|$, which is less than zero degrees, and in an opposite direction from an angle of zero degrees to an angle $+|\alpha_2|$, which is greater than zero degrees, with respect to said longitudinal axis of said tubular shaft.

2. The instrument of claim 1, wherein said joint is a hinge-like joint.

3. The instrument of claim 1, wherein said angles $|\alpha_1|$ and $|\alpha_2|$ are substantially equal.

4. The instrument of claim 1, wherein said angles $|\alpha_1|$ and $|\alpha_2|$ are different.

5. The instrument of claim 1, wherein at least a portion of said tubular shaft secured to said distal end portion is rotatable with respect to said manipulating means about said longitudinal axis of said tubular shaft.

6. The instrument of claim 1, wherein said distal end portion is formed as a tube piece which is directly adjacent to said remaining portion of said tubular shaft.

7. The instrument of claim 6, wherein said distal end portion and said remaining portion of said tubular shaft form a V in the region of said joint, wherein at a tip of said V said joint connection is established.

8. The instrument of claim 1, wherein said distal end portion has an axial length which is only slightly larger than an outer diameter of the remaining tubular shaft.

9. The instrument of claim 1, wherein said distal end portion has substantially the same outer diameter as said remaining portion of said tubular shaft.

10. The instrument of claim 1, wherein the outer diameter of said tubular shaft is in the range of 2 to 10 mm.

11. The instrument of claim 1, wherein said distal end portion comprises a fixing sleeve for fixing said light-emitting end of said light waveguide.

12. The instrument of claim 1, wherein said tubular shaft comprises a connector for connecting said tubular shaft with a suction and/or irrigation device.

13. The instrument of claim 1, wherein the interior of said tubular shaft comprises an irrigation passage.

14. The instrument of claim 1, wherein said distal end portion comprises openings distributed about its circumference for irrigating.

15. The instrument of claim 14, wherein said openings are disposed at a front face and at axially extending sides of the distal end portion.

16. The instrument of claim 1, wherein said manipulating means are configured in the form of a scissors-like handle arrangement.

17. The instrument of claim 1, wherein said actuator element is configured as a wire push and pull element, which runs through the interior of said tubular shaft.

18. The instrument of claim 1, wherein said actuator element is formed as an inner tubular shaft arranged to be axially shiftable within said tubular shaft with said light waveguide being insertable in the interior of said inner tubular shaft.

19. The instrument of claim 1, wherein said actuator element is articulated to said distal end portion at an articulation point which is radially spaced from said joint of said distal end portion by a distance which is substantially equal to an outer diameter of said tubular shaft.

20. The instrument of claim 1, wherein said pivotal motion of said pivotal distal end portion is limited to a predetermined angular range.

21. The instrument of claim 20, wherein the limit of pivotal motion is adjustable by an adjustable stop on said manipulating means.

22. The instrument of claim 1, wherein said distal end portion can be locked into a plurality of discrete angular positions with respect to said longitudinal axis of said tubular shaft.

23. The instrument of claim 22, wherein said at least one movable operating element of said manipulating means is engageable with a toothed bracket having a plurality of locking positions.

24. The instrument of claim 23, wherein teeth of said toothed bracket are rounded.

25. The instrument of claim 1, wherein said distal end portion is rounded.

26. The instrument of claim 1, wherein the interior of said tubular shaft comprises a suction passage.

27. The instrument of claim 1, wherein said distal end portion comprises openings distributed about its circumference for suctioning.

28. The instrument of claim 1, wherein said actuator element is configured as a rod push and pull element, which runs through the interior of said tubular shaft.

29. The instrument of claim 1, wherein said distal end portion can be locked into a plurality of continuous angular positions with respect to said longitudinal axis of said tubular shaft.

* * * * *